(12) United States Patent
Bienvenut et al.

(10) Patent No.: US 6,632,339 B1
(45) Date of Patent: Oct. 14, 2003

(54) METHOD OF IDENTIFYING POLYPEPTIDES

(75) Inventors: Willy Vincent Bienvenut, Thenac (FR); Denis Francois Hochstrasser, Geneva (CH)

(73) Assignee: University of Geneva, Geneva (CH)

( * ) Notice: Subject to any disclaimer, the term of this patent is extended or adjusted under 35 U.S.C. 154(b) by 204 days.

(21) Appl. No.: 09/594,906

(22) Filed: Jun. 15, 2000

Related U.S. Application Data (62) Division of application No. 09/107,991, filed on Jun. 30, 1998, now Pat. No. 6,221,626.

(51) Int. Cl.$^7$ .................. B01D 57/02; B01D 59/42; B01D 59/50; C02F 1/40; C12Q 1/00
(52) U.S. Cl. .................. 204/462; 204/464; 204/613; 204/614; 435/4
(58) Field of Search .................. 204/464, 462, 204/613, 614; 435/4

(56) References Cited

U.S. PATENT DOCUMENTS

| | | | |
|---|---|---|---|
| 5,595,636 A | 1/1997 | Franzen | |
| 5,719,060 A | 2/1998 | Hutchens et al. | |

FOREIGN PATENT DOCUMENTS

| | | |
|---|---|---|
| DE | 4408034 | 7/1995 |

OTHER PUBLICATIONS

Schleuder et al Anal Chem 1999 vol. 71(15) pp. 3238–3247.*
Rowe et al. (Nature 1997 vol. 388 pp. 292–295).*
Su et al. (Cell 1995 vol. 82 pp. 89–100).*
Baruch et al. (PNAS 1996 vol. 93 pp. 3497–3502).*
M. Kussman et al., "Characterisation of the covalent structure of proteins from biologial material", Spectroscopy (Folume No. not known) 1–27 (1998).
K.S. Ha et al., "Atmospheric Biosensor for Urea", Bulletin of the Korean Chemical Society 18(11), pp. 114–115 (1997).
M.L. Seo et al., "Amperometric Enzyme Electrode for the determination of NH4+", Journal of the Korean Chemical Society 37 (11) pp. 937–939 (1993); from http://www.kcs.korea.ac.kr/publi/dh/dh93n11/dh93n11.html.
T. Morcal et al., "Dot–blot analysis of the degree of covalent . . . ", J. Immunol. Methods 203 (1), 45–53 (1997).
B. Canas et al., "Covalent attachment of peptides to membranes . . . ", Analytical Biochemistry 211, 179–182 (1993).
C. Viera, Biotechnology Training Program, University of Wisconsin–Madison, from http://www.bact.edu/biotech/viera.htm.
M. Schreisner et al., Ultraviolet matrix assisted laser desorption ionization–mass spectrometry of electroblotted proteins Electrophoresis 17, 954–961 (1996).
J.M. Coull et al., "Development of membrane supports for the solid–phase sequennce analysis of proteins and peptides" in "Methods in Protein Sequence Analysis", Ed. B. Wittman–Leibold, Springer–Verlag, Berlin (1989), pp. 69–78.
J.M. Coull et al., "Functionalized membrane support for covalnt protein microsequence analysis", Anal. Biochem. 194, 110–120 (1991).
MSI Technical Bulletin 633, Transfer of high molecular weight proteins from a non–denaturing gel system.
D.J.C. Pappin et al., "New approaches to covalent sequence analysis" in "Current Research in Protein Chemistry: Techniques, Structure and Fluction", Ed. J.J. Villa–franca, Acad. Press, San Francisco and London (1990), pp. 191–202.
MSI Technical Bulletin 633, "Transfer of high molecular weight proteins from a non–denaturing gel to the MSI PVDF–plus membrane" (Jun. 19, 1997), from http://www.msifilters.com/tb633.txt.
W. Bienvenut et al., "Towards the automation of protein analysis by mass spectrometry", Poster P13 and Abstract, Electrophorese Forum '97–Strasbourg (Nov. 25–27, 1997).
Analytical Sciences vol. 7 Supplement 1991, "Microsequence Analysis of $N^\alpha$–Blocked Proteins Electroblotted Onto An Immobilizing Matrix From Polyacrylamide Gels."
Hasselberger, "Uses of Enzymes and Immobilized Enzymes", Welson–Hall, Chicago 1978, pp. 23, 24 & 29.
Creighton, T.E., "Protein Structure a Practical Approach", MRC Laboratory of Molecular Biology, Cambridge, UK.

* cited by examiner

Primary Examiner—Mark Navarro
(74) Attorney, Agent, or Firm—Baker Botts LLP (57) ABSTRACT

Polypeptides which have been separated by gel electrophoresis can be identified by electroblotting them through a "sandwich" comprising in order:
  a) the separation gel;
  b) at least one hydrophilic membrane, e.g. of carboxyl-modified PVDF, on which is immobilized at least one reagent capable of cleaving a polypeptide, e.g. trypsin;
  c) a hydrophobic layer, typically a membrane, e.g. of PVDF.

Preferably a biased alternating current or discontinuous direct current is used for electroblotting. The resulting fragments, usually peptides, are identified, preferably by MALDI-TOF MS.

9 Claims, 3 Drawing Sheets

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
         (A) LENGTH: 14 amino acids
         (B) TYPE: amino acid
         (C) STRANDEDNESS: <Unknown>
         (D) TOPOLOGY: linear      (ii) MOLECULE TYPE: peptide      (v) FRAGMENT TYPE: internal      (xi) SEQUENCE DESCRIPTION: SEQ ID NO: 1:

Arg Ala Phe His Thr Thr Gly Arg Ile Ile Ala Gly Ala Glu
1             5                  10

(2) INFORMATION FOR SEQ ID NO: 2:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear     (ii) MOLECULE TYPE: peptide      (v) FRAGMENT TYPE: internal     (xi) SEQUENCE DESCRIPTION: SEQ ID NO: 2:

```
Ser His Ser Ala Asp Val Arg Ala Phe His Thr Thr Gly Arg Ile Ile
1               5                  10                  15

Ala Gly Ala Glu
            20
```

(2) INFORMATION FOR SEQ ID NO: 3:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear     (ii) MOLECULE TYPE: peptide      (v) FRAGMENT TYPE: internal     (xi) SEQUENCE DESCRIPTION: SEQ ID NO: 3:

```
Cys Pro Leu Thr Val Val Gln Ser Arg
1               5
```

(2) INFORMATION FOR SEQ ID NO: 4:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear     (ii) MOLECULE TYPE: peptide      (v) FRAGMENT TYPE: internal     (xi) SEQUENCE DESCRIPTION: SEQ ID NO: 4:

```
Gly Ile Gly Thr Ile Ile Ser Ser Pro Tyr Arg
1               5                  10
```

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear     (ii) MOLECULE TYPE: peptide      (v) FRAGMENT TYPE: internal     (xi) SEQUENCE DESCRIPTION: SEQ ID NO: 5:

```
Asn Lys Pro Leu Val Val Gln Phe Gln Lys
1               5                  10
```

(2) INFORMATION FOR SEQ ID NO: 6:

(i) SEQUENCE CHARACTERISTICS:
           (A) LENGTH: 13 amino acids
           (B) TYPE: amino acid
           (C) STRANDEDNESS: <Unknown>
           (D) TOPOLOGY: linear (ii) MOLECULE TYPE: peptide (v) FRAGMENT TYPE: internal (xi) SEQUENCE DESCRIPTION: SEQ ID NO: 6:

Ile Arg Phe Ile Ala Glu Gly His Pro Leu Ser Leu Lys
1               5                  10

(2) INFORMATION FOR SEQ ID NO: 7:

(i) SEQUENCE CHARACTERISTICS:
           (A) LENGTH: 13 amino acids
           (B) TYPE: amino acid
           (C) STRANDEDNESS: <Unknown>
           (D) TOPOLOGY: linear (ii) MOLECULE TYPE: peptide (v) FRAGMENT TYPE: internal (xi) SEQUENCE DESCRIPTION: SEQ ID NO: 7:

Ile Gly Glu Asn Lys Asp Ala Asn Asp Gly Trp Phe Arg
1               5                  10

(2) INFORMATION FOR SEQ ID NO: 8:

(i) SEQUENCE CHARACTERISTICS:
           (A) LENGTH: 16 amino acids
           (B) TYPE: amino acid
           (C) STRANDEDNESS: <Unknown>
           (D) TOPOLOGY: linear (ii) MOLECULE TYPE: peptide (v) FRAGMENT TYPE: internal (xi) SEQUENCE DESCRIPTION: SEQ ID NO: 8:

Asn Glu Leu Asp Lys Gly Ile Gly Thr Ile Ile Ser Ser Pro Tyr Arg
1               5                  10                  15

(2) INFORMATION FOR SEQ ID NO: 9:

(i) SEQUENCE CHARACTERISTICS:
           (A) LENGTH: 30 amino acids
           (B) TYPE: amino acid
           (C) STRANDEDNESS: <Unknown>
           (D) TOPOLOGY: linear (ii) MOLECULE TYPE: peptide (v) FRAGMENT TYPE: internal (xi) SEQUENCE DESCRIPTION: SEQ ID NO: 9:

Asp Phe Val Leu Asp Asn Glu Gly Asn Pro Leu Glu Asn Gly Gly Thr
1               5                  10                  15

Tyr Tyr Ile Leu Ser Asp Ile Thr Ala Phe Gly Gly Ile Arg
                20                  25                  30

(2) INFORMATION FOR SEQ ID NO: 10:

(i) SEQUENCE CHARACTERISTICS:
           (A) LENGTH: 10 amino acids
           (B) TYPE: amino acid
           (C) STRANDEDNESS: <Unknown>

(D) TOPOLOGY: linear (ii) MOLECULE TYPE: peptide (v) FRAGMENT TYPE: internal (xi) SEQUENCE DESCRIPTION: SEQ ID NO: 10:

Ala Ala Cys Gly Ile Thr Asn Lys Pro Lys
1               5                  10

(2) INFORMATION FOR SEQ ID NO: 11:

(i) SEQUENCE CHARACTERISTICS:
          (A) LENGTH: 16 amino acids
          (B) TYPE: amino acid
          (C) STRANDEDNESS: <Unknown>
          (D) TOPOLOGY: linear (ii) MOLECULE TYPE: peptide (v) FRAGMENT TYPE: internal (xi) SEQUENCE DESCRIPTION: SEQ ID NO: 11:

Arg Glu Leu Gln Leu Val Gly Ile Ser Ala Met Leu Met Ala Ser Lys
1               5                  10                  15

(2) INFORMATION FOR SEQ ID NO: 12:

(i) SEQUENCE CHARACTERISTICS:
          (A) LENGTH: 28 amino acids
          (B) TYPE: amino acid
          (C) STRANDEDNESS: <Unknown>
          (D) TOPOLOGY: linear (ii) MOLECULE TYPE: peptide (v) FRAGMENT TYPE: internal (xi) SEQUENCE DESCRIPTION: SEQ ID NO: 12:

Leu His Thr Gly Tyr Ser Gln Glu Gln Leu Met Asp Cys Ala Arg Leu
1               5                  10                  15

Leu Val Gly Phe Tyr Ser Thr Leu Glu Asn Gly Lys
                20                  25

(2) INFORMATION FOR SEQ ID NO: 13:

(i) SEQUENCE CHARACTERISTICS:
          (A) LENGTH: 13 amino acids
          (B) TYPE: amino acid
          (C) STRANDEDNESS: <Unknown>
          (D) TOPOLOGY: linear (ii) MOLECULE TYPE: peptide (v) FRAGMENT TYPE: internal (xi) SEQUENCE DESCRIPTION: SEQ ID NO: 13:

Asn Lys Pro Leu Val Val Gln Phe Gln Lys Leu Asp Lys
1               5                  10

(2) INFORMATION FOR SEQ ID NO: 14:

(i) SEQUENCE CHARACTERISTICS:
          (A) LENGTH: 17 amino acids
          (B) TYPE: amino acid
          (C) STRANDEDNESS: <Unknown>
          (D) TOPOLOGY: linear (ii) MOLECULE TYPE: peptide -continued (v) FRAGMENT TYPE: internal (xi) SEQUENCE DESCRIPTION: SEQ ID NO: 14:

Ala Ala Pro Thr Gly Asn Glu Arg Cys Pro Leu Thr Val Val Gln Ser
1               5                   10                  15
Arg (2) INFORMATION FOR SEQ ID NO: 15:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear     (ii) MOLECULE TYPE: peptide     (v) FRAGMENT TYPE: internal     (xi) SEQUENCE DESCRIPTION: SEQ ID NO: 15:

Cys Gly Asp Ile Gly Ile Ser Ile Asp His Asp Asp Gly Thr Arg Arg
1               5                   10                  15

METHOD OF IDENTIFYING POLYPEPTIDES

This application is a divisional of U.S. patent application Ser. No. 09/107,991, filed Jun. 30, 1998 now U.S. Pat. No. 6,221,262.

BACKGROUND OF THE INVENTION

1. Field of the Invention

This invention relates to the identification of polypeptides which have been separated on the same gel, typically from polyacrylamide gel electrophoresis (PAGE) and to a kit for use in the method. It is especially useful in proteomics (the large scale identification and characterization of proteins).

2. Description of the Related Art

In proteomics, massively parallel protein identification and characterization techniques are required. The identification of proteins or other polypeptides merely by PAGE, even using two-dimensional gels (2D-PAGE), is laborious and often uncertain. Many different methods have been developed to identify and partially characterize proteins from complex biological samples. Some of them use Matrix Assisted Laser Desorption Ionization-Time of Flight (MALDI-TOF) techniques to analyze peptide "fingerprints" produced by fragmenting the proteins with enzymes. Several software programs have been developed to compare mass spectra of the peptides obtained from MALDI-TOF experiments with theoretical spectra from proteins. The subject has been reviewed by Kussmann and Roepstorff [1]. These authors noted three ways in which proteins separated by gel electrophoresis could be digested with enzymes to yield fragment peptides:

1. The digestion can be carried out in a plug of excised gel and the peptides recovered by elution. This is the authors' own preference.
2. The protein can be first electroleluted from an excised gel plug and then digested in solution.
3. The protein can be electroblotted onto a membrane and subsequently digested on the membrane.

These types of processes are not practical for the sequencing of polypeptides which have been run on the same gel, since the cutting out of the polypeptide bands from the gel has to be done sequentially and the plugs thus obtained placed in tubes for further analysis. Also, losses occur when the polypeptides adhere to the walls of the tube.

SUMMARY OF THE INVENTION

The present invention provides a solution to the above problem. It has now been found that the proteins or other polypeptides separated on a gel can be cleaved into fragments, for example by digestion with an enzyme, and these fragments presented very satisfactorily for analysis, especially by MALDI-TOF MS, if the cleaving agent is immobilized and interposed as the "filling" in an electroblotting "sandwich" between the separation gel as one "slice" of the sandwich and a collection layer, exemplified as a conventional PVDF membrane, as the other "slice" of the sandwich. In this way, the fragments are collected on the hydrophobic layer and can then be formulated in an appropriate way for the MALDI-TOF MS. It is only necessary that the electroblotting is carried out so that the proteins have a long enough residence period in the proximity of the immobilized cleaving agent to ensure that a reasonable amount of the fragments is produced, but, of course, not so long as to allow undesired diffusion. This is easily achievable by varying appropriately the current used in the electroblotting, e.g. by pulsing the current or using a unsymmetrical alternating current. Further, when an enzyme is used as the cleaving agent and when the enzyme is immobilized securely on the hydrophilic membrane, especially by covalent bonding to the solid phase, autodigestion (cleavage of the enzyme by itself) is inhibited.

According to a specific aspect of the invention there is provided a method of identifying polypeptides which have been separated on the same gel by electrophoresis, comprising the steps of:

a) providing adjacent to the gel at least one hydrophilic membrane on which is immobilized at least one reagent capable of cleaving a polypeptide;

b) providing a hydrophobic collection layer suitable for receiving thereon fragments of polypeptide transferred thereto by electroblotting, said hydrophobic layer being positioned beyond the hydrophilic membrane in a direction of movement of the fragments of polypeptide (usually cathode to anode);

c) electroblotting the polypeptides from the separation gel through the hydrophilic membrane or membranes, under conditions effective to cause the polypeptides to be cleaved into fragments by the cleaving reagent, to the hydrophobic layer; and d) identifying the fragments collected on the hydrophobic layer and from the identification of the fragments, identifying the polypeptide from which they came.

In another aspect, the invention provides a membrane suitable for use in an electroblotting sandwich, having immobilized thereon at least one polypeptide-cleaving reagent, especially a modified PVDF membrane having a protease, especially trypsin, covalently bonded thereto.

The invention further includes a kit for use in the method of the invention, said kit comprising:

a) at least one hydrophilic membrane on which is immobilized at least one reagent capable of cleaving a polypeptide; and b) a hydrophobic collection layer suitable for receiving thereon fragments of polypeptide transferred thereto by electroblotting.

The term "kit" as used herein includes combinations of the identified components in separate containers and also an assembly of the hydrophilic membrane(s) and hydrophobic collection layer ready for use. The kit may further include reagents useful in the method of the invention, e.g. electroblotting buffer, reagent(s) which assist in the reaction of the enzyme with the polypeptide fragment and so on.

The term "collection layer" as used herein has a broad meaning, since this is not in itself critical to the invention. It may be in isolation self-supporting or non-self-supporting and can be a membrane, film, coating or plate. It will normally be porous to the electroblotting buffer, to enable current to be carried to or from the electrode, but may alternatively be the electrode or in direct electrical communication with it.

The term "identifying" as used herein is not synonymous with determining the sequence and includes partially identifying the polypeptide or characterizing it as similar to or different from a known protein. Further it includes making a tentative identification based on the most probable of a small number of possibilities.

DESCRIPTION OF THE PREFERRED EMBODIMENTS

The invention relates to identifying polypeptides which have already been separated by gel electrophoresis. The nature of the polypeptides to be identified is not critical. They can be, for example, naturally occurring proteins, proteins made by recombinant DNA technology, polypeptides made by peptide synthesis or by expression of recombinant DNA. For brevity, the invention will be described hereinafter with reference to proteins. The extrapolation to other polypeptides will be taken as understood and incorporated throughout the following description.

The kind of gel on which the proteins have been separated is not critical, but will usually be a polyacrylamide gel. Any of the conventional gels and separation conditions may have been employed, including reducing conditions. They may be one-dimensional or two-dimensional gels. (In 2D gels, proteins etc. are separated in one dimension by their charge and in the other dimension by their molecular mass).

The invention is to be applied to multiple proteins co-present on the gel, for example from 3 to 3000, more usually 30 to 3000 and preferably 50 to 1500, proteins. This includes proteins present at different molecular weight separations on a 1D gel or at similar molecular weight separations, but present in parallel lanes or tracks on the 1D gel, as well as those separated by 2D gel electrophoresis.

Figure 1:
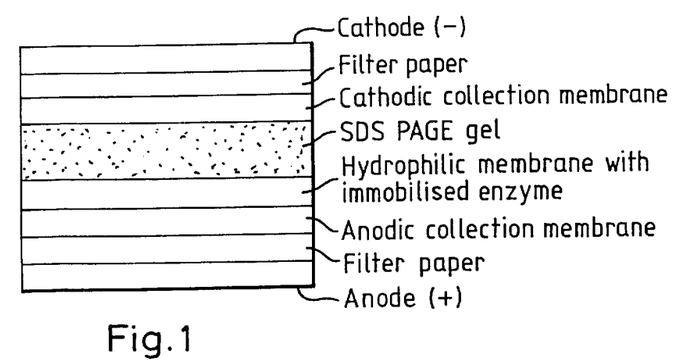
FIGS. 1 and 2 are schematic views of two kinds of blotting "sandwich" which can be used in the invention.
Figure 2:
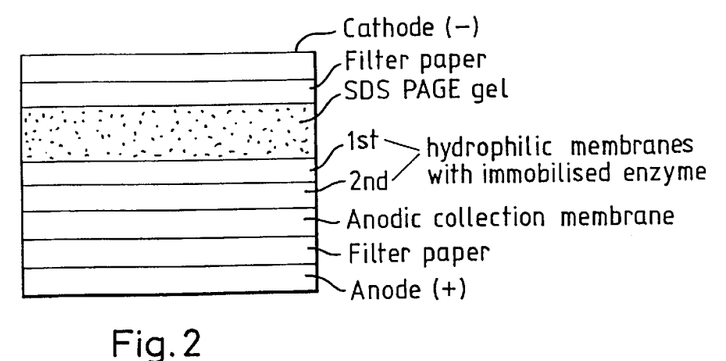

Normally, the electroblotting takes place overall in the direction cathode to anode, as the proteins are negatively charged. Depending on the pH of the electroblotting buffer used, positively and negatively charged fragments could be obtained and migrate in opposite directions, towards the cathode and anode respectively. FIGS. 1 and 2 of the drawings exemplify some sandwiches for the electroblotting. FIG. 1 shows an experimental arrangement in which a cathodic collection layer, which is preferably a conventional PVDF membrane, was provided, just to show that under these conditions no proteins migrated to this membrane, despite the alternating field applied (thus reversing the electrodes). It will be understood that under different pH conditions, some fragments could be produced at the cathodic collection layer. Thus, the invention includes the possibility of providing anodic and cathodic collection layers, with hydrophilic membranes interposed between each of them and the separation gel layer. In FIG. 1 there is a single hydrophilic membrane, which is preferably a modified PVDF membrane, having an appropriate protein-cleaving reagent, normally a protease enzyme, for example trypsin, immobilized on it, interposed between the gel layer and an anodic collection layer, most conveniently a conventional PVDF membrane, on which the protein fragments are collected. In FIG. 2 there is no cathodic collection layer, but there are two consecutive hydrophilic membranes, preferably modified PVDF membranes, each with trypsin immobilized thereon, placed between the gel layer and the anodic collection layer, which, again, is preferably a conventional PVDF membrane.

In more detail, the anode and cathode are separated from the rest of the sandwich by an absorptive layer which soaks up the blotting liquid, while maintaining the liquid in electrical contact with the electrodes, and is conveniently a filter paper. The kinds of electrodes and absorptive layers used in arrangement are not critical and can be any conventionally used in electroblotting.

The anodic collection layer (and cathodic collection layer if used) are also not critical and thus can be any conventional hydrophobic membrane used in electroblotting, such as PVDF, nylon or nitrocellulose, for example.

The "filling" of the sandwich can take the form of one or more membranes (defined as above) sufficiently hydrophilic in character that the proteins and fragments thereof do not tend to stick thereon. This membrane can be any layer which is porous to the electroblotting liquid and capable of immobilizing the polypeptide-cleaving reagent thereon, whether on the surface thereof of within interstices or microcavities therein accessible to the electroblotting liquid (and therefore to the polypeptide to be cleaved). It will typically be from 100 to 600 $\mu$m thick. Usually the number of such membranes will be from 1 to 3. With conventional thicknesses of membrane, e.g. 130 to 150 $\mu$m as in the preferred "Immobilon AV" PVDF membrane, 2 membranes will frequently be used. They are best placed directly mutually adjacent, i.e. one on top of another. The hydrophilic membrane(s) are preferably provided with "active carbonyl" or carboxylic acid groups or derivatives thereof reactive with amino groups present in enzymes. "Active carbonyl"-modified or carboxyl-modified PVDF membranes are especially preferred.

Since it would be difficult to react all the active groups present on the surface of a membrane with an enzyme, and since it is undesirable to allow the polypeptides to react with these free active groups, the residual active groups (which would otherwise be free) are preferably capped before the membrane is used, e.g. with ethanolamine, thus providing terminations such as —CO—NH—CH$_2$—CH$_2$—OH, which are relatively hydrophilic. Other hydrophilic capping groups will suggest themselves to those skilled in the art.

Alternatively, PVDF membranes or glass fiber paper can be functionalized by isothiocyanate, which allows reaction with the E-amino groups of lysine residues in the enzymes. For this purpose, the PVDF membranes are pre-treated with NaOH to provide a carbon-carbon ethylenic double bond in the polymer chain (by elimination of a molecule of HF [12]). The pre-treated PVDF membranes are then reacted under basic conditions with a dinucleophile such as ethylenediamine, 1,10-diaminodecane or 2-aminoethanethiol, whereby hydrogen atoms in the polymer are substituted by —X—(CH$_2$)$_n$—NH$_2$ groups, wherein —X— is —S— or —NH— and n is 2 or 10. This polymer, having amine-terminated side-chains, is then reacted with 1,4-phenylenediisothiocyanate (DITC) or 3,5-dichloro-1,4-phenylenediisocyanate (DCDITC) to give the required isothiocyanate-terminated side-chains in good yield. DITC-reacted glass fiber sheets provide another form of membrane [3].

Another form of membrane is PVDF functionalized by arylamine groups, which react with a carboxylic acid side-chain or the carboxyl terminus of the enzyme, preferably in the presence of a carbodiimide such as 1-(3-dimethylaminopropyl)-3-ethylcarbodiimide.

Another form of hydrophilic membrane which can be used as the sandwich filling is a thin film or coating of agarose gel. The ε-amino groups of lysine residues in the enzyme are treated to obtain aminoxy groups, which react with aldehyde groups produced by mild oxidation of the agarose gel, thus bonding the enzyme covalently to the agaraose.

A further kind of hydrophilic membrane may comprise one or more thin films or coatings of polyacrylamide gel, similar in thickness to that used in immobilized pH gradient electrophoresis (IPG), but which has been trypsinated. This can be done by reacting trypsin with acryloyl chloride to form an N-acryloyltrypsin, which is then copolymerized with acrylamide in the preparation of an acrylamide copolymer gel.

Yet another form of hydrophilic membrane is a glass fiber paper which has been modified to replace amino groups by groups containing a diazo linkage, e.g. 4-N,N-dimethylaminoazobenzene-4'-isocyanato groups. The reactions required for this purpose have been described [5].

The cleavage reagent is normally and preferably immobilized by covalent bonding. However, other forms of immobilization are not excluded from use in this invention, so long as the enzyme does not become sufficiently free in solution in the electroblotting liquid as to undergo autodigestion. (It will be understood that the presence of autodigested enzyme fragments could upset the analysis of the fragments from the protein to be analyzed). Thus, for example, the enzyme could be physically trapped within the pores of a porous sheet of hydrophilic polymer. Alternatively, the membrane could have an enzyme immobilized thereon by means comprising (consisting of or including) affinity bonding. Thus, the enzyme could be covalently attached to avidin or streptavidin and the resultant conjugate attached to a biotinylated membrane by affinity bonding between avidin/streptavidin and biotin. Alternatively, avidin or streptavidin could be attached to the membrane and the enzyme could be reacted to provide biotinyl terminations for reaction with a membrane to which avidin or streptavidin has been attached.

Preferably the cleavage agent will be an enzyme and most preferably and usually one which cleaves the main chain of the polypeptide, especially trypsin. Trypsin cuts proteins at the C-terminal end of many lysines and arginines. Other less specific endoproteases, e.g. pepsin or such as chymotrypsin are usable, as are the highly specific, lys-C, arg-C or glu-C. For phosphoproteins, a phosphorylase is useful. The enzyme can be one which splits off a side-chain of the protein. More than one enzyme can be immobilized on the membrane. For example, it may be helpful to split off one or more side chains of the polypeptide, e.g. using a carboxypeptidase or aminopeptidase in conjunction with an endoproteinase. Carboxypeptidase Y is one particularly useful such enzyme.

To investigate the presence of side-chains in proteins, such as glucosyl, N-acetyl-O-glucosaminyl and sialyl, enzymes which will cleave those chains, such as glucosidase, N-acetylglucosaminidase and neuraminidase, respectively, are useful in the invention.

The cleavage reagent is not confined to enzymes, but could be a chemical reagent, for example cyanogen bromide, physically immobilized by entrapment within a porous matrix.

The electrical current applied in the electroblotting is preferably not a direct, continuous current, but either pulsed, i.e. a direct current with intervals in which no current is passed, or an alternating current biased in the cathode to anode direction, i.e. mainly a cathode to anode current, but with intervals in which current is passed in the opposite direction. Variations on these regimes are possible within the general spirit of the idea of performing a slower than normal electroblotting, allowing time for the cleavage to take place on the hydrophilic membrane(s), while not causing so much delay in the travel of the proteins and fragments from the separation gel to the collection membrane that would cause undue lateral (sideways) diffusion, causing loss of resolution.

The electroblotting liquid is not critical, but is preferably buffered and can be any conventional buffer for this purpose, such as Tris/glycine with methanol or 3-(cyclohexylamino)-1-propanesulfonic acid (CAPS) with methanol. The direction of migration of the fragments depends essentially on the pH of the buffer. For most purposes an alkaline buffer will be appropriate, since many enzymes function best at alkaline pH. Some, however, such as endoproteinase V8, require an acidic pH. Under such conditions, the fragments will migrate to the cathode.

The protein fragments, whether they are peptides derived from the main chain of the protein or are residues of a side-chain, are collected on the collection layer. They are then preferably analyzed by MALDI-TOF MS in a conventional way. This involves forming a matrix on the membrane, e.g. as described in the literature [1], with an agent which absorbs the incident light strongly at the particular wavelength employed. The sample is excited by UV, or IR laser light into the vapor phase in the MALDI mass spectrometer. Ions are generated by the vaporization and form an ion plume. The ions are accelerated in an electric field and separated according to their time of travel along a given distance, giving a mass/charge (m/z) reading which is very sensitive. MALDI spectrometers are commercially available and are described in the literature [1].

In this invention, the above method is applied to the scanning of the fragments of many proteins at once. Thus, many proteins can be run simultaneously on a polyacrylamide gel, subjected to the method of the invention to produce an array of spots on the collecting membrane and the array analyzed as follows. After the PVDF membrane or other hydrophobic layer has been stained, a piece of it will be cut and fixed on the MALDI-MS sample plate, e.g. with silicone grease. An organic matrix-forming reagent is added to the membrane on the sample plate and the sample is then air-dried to form the matrix. The sample plate is inserted in the MALDI-MS spectrometer. An automated movement of the sample plate from a first to a second position is arranged by computer program. At each position a MALDI-MS spectrum is generated, the spectral information collected in digital form and the data downloaded to the ExPASy database research program (PeptIdent).

It is then simple to provide automated output of the results by using the ExPASy server, as at present used for MALDI-TOF MS and to generate the data in a form handleable by computers.

It will be evident, therefore, that the present invention has huge potential for the automated identification and/or partial characterization of proteins, e.g. in proteomics research. In effect, the invention provides in this preferred embodiment a "molecular scanner" for this purpose.

Other methods can be used to analyze the fragments of protein obtained on the collection membrane. These include mass spectrometry, which can include other forms of time of flight mass spectrometry, e.g. liquid chromatography triple quadruple MS, Q-TOF ion trap, or MS-MS. Still other methods of analysis comprise Western blotting against specific peptides and phospho-imaging.

The invention also relates to materials useful in the above method. The immobilization of enzymes on membranes is not in itself new, since it is known to co-immobilize L-glutamate dehydrogenase and urease onto an "Immobilon AV" PVDF membrane attached to a glass electrode, as an amperometric biosensor for urea [4]. However, it is believed new to immobilize polypeptidecleaving enzymes, especially trypsin, on membranes, especially on modified PVDF membranes, which therefore form part of the invention.

Optionally, other components may be sold together with the hydrophilic membrane(s), especially any one or more of the following: matrix-forming reagent for MALDI-TOF, electroblotting buffer, collection layer(s), preferably PVDF, and PAGE materials. Kits comprising the membrane(s) and any one, two or more of the above optional components are hereby specifically declared to be within the invention. The components of the kit may be supplied in separate containers, but packaged overall as a kit.

The following Examples illustrate the invention. The words "Immobilon", "Trans-Blot", "Tween" and "Voyager" are Registered Trade Marks.

EXAMPLES

Materials and Methods

Chemicals. "Immobilon" type AV membranes were purchased from Millipore (Bedford, Mass., USA) [2]. Acrylogel-PIP 2.6 (2,6-diacryloylpiperidine) solution was purchased from BDH (Poole, England). Low range SDS-PAGE standard PVDF membranes were purchased from Bio-Rad (Richmond, Calif., USA). Trifluoroacetic acid (TFA), Tris and trypsin (type IX from porcine pancreas, dialyzed and lyophilized) were purchased from Sigma (St-Louis, Mo., USA). Acetonitrile (preparative HPLC grade), calcium chloride, ethanolamine glycine and α-Tosyl-L-arginine methyl ester (TAME) were purchased from Fluka (Buch, Switzerland).

1-D and 2-D PAGE. For the 1-D PAGE method, Mini-Protean II electrophoresis apparatus (Bio-Rad, Richmond, Calif., USA) was used. SDS-PAGE was conducted essentially according to the method of Laemmli [6] with 12%T and 2.6%C polyacrylamide gel. The protein samples used were commercially available SDS-PAGE standards. They were chicken lysozyme (14.3 KDa), soybean trypsin inhibitor (20.1 KDa), bovine carbonic anhydrase (28.9 KDa), chicken ovalbumin (42.7 KDa), bovine serum albumin (66.4 KDa), and rabbit phosphorylase Y) (97.2 KDa). Protein migration was carried out on a single lane at 200 V for 40–50 minutes.

For the 2-D PAGE method, protein separation from the sample can be conducted according the method previously described by Hochstrasser et al. [7–9] and Sanchez et al. for mini 2-D PAGE [10].

Covalent attachment of trypsin and blockage of the IAV membrane. IAV membrane is a new commercially available modified PVDF membrane, having activated carboxylated groups. These groups are reactive towards nucleophiles such as amine groups from proteins or peptides. Based on the above-cited Millipore technical documentation on "Immobilon AV", trypsin was immobilized on this membrane (FIG. 1).

A 10×12 cm IAV membrane was incubated in a rotating hybridizer HB-2D (Techne, Cambridge, England) with 20 ml of a 2.5 mg/ml trypsin solution in 20 mM sodium dihydrogen phosphate buffer, pH 7.8, at room temperature for 3 hours. Then, the membrane was washed 3 times rapidly and vigorously with 20 ml of PBS-"Tween" 20 solution (20 mM of sodium dihydrogen phosphate, 140 mm sodium chloride and 0.5% "Tween" 20, pH 7.4) to remove unreacted trypsin. The membrane was incubated for 3 hours with 20 ml of 1M ethanolamine in 1M sodium bicarbonate, pH 9.5, at 4° C. to block the remaining active carboxyl groups of the membrane. After this capping step, the membrane was washed 3 times rapidly and vigorously with 20 ml of the PBS-"Tween" solution and then twice for 30 minutes with 20 ml of the PBS-"Tween" solution. The membranes were stored at 4° C. in a 460 mM Tris-HC1, 11.5 mM calcium chloride buffer solution, pH 8.1.

Activity measurement of the bioenzyme covalently bound to the IAV membrane. The tryptic activity of the IAV-Trypsin membrane was determined using the trypsin assay reagent TAME [11]. One to 2 $cm^2$ of the IAV-trypsin membrane was immersed in a mixture composed of 2.6 ml of 460 mM Tris-HC1, 11.5 mM calcium chloride, pH 8.1, 0.3 ml of 10 mM TAME solution and 0.1 ml of 1 mM HCl solution. After 40 seconds of vigorous stirring, the absorbance of the solution was measured at 247 nm with a UV-Visible spectrophotometer (Ultrospec III, Pharmacia Biotech, Uppsala, Sweden). A second measurement was made after 3 minutes of constant stirring. The equivalent amount of free active trypsin per surface unit was calculated from the value of the change in optical absorbance ($A_{247}$/min) as described previously [11].

Figure 3:
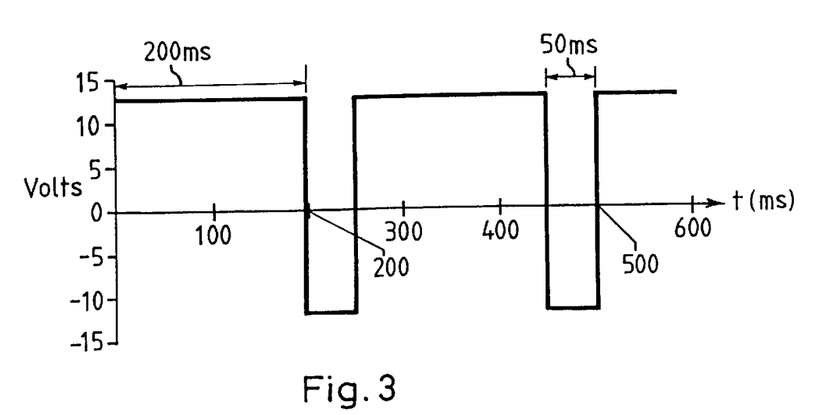
FIG. 3 is a plot of applied voltage against time, showing the production of an unsymmetrical or biased alternating voltage for use in electroblotting in the method of the invention.
Figure 4:
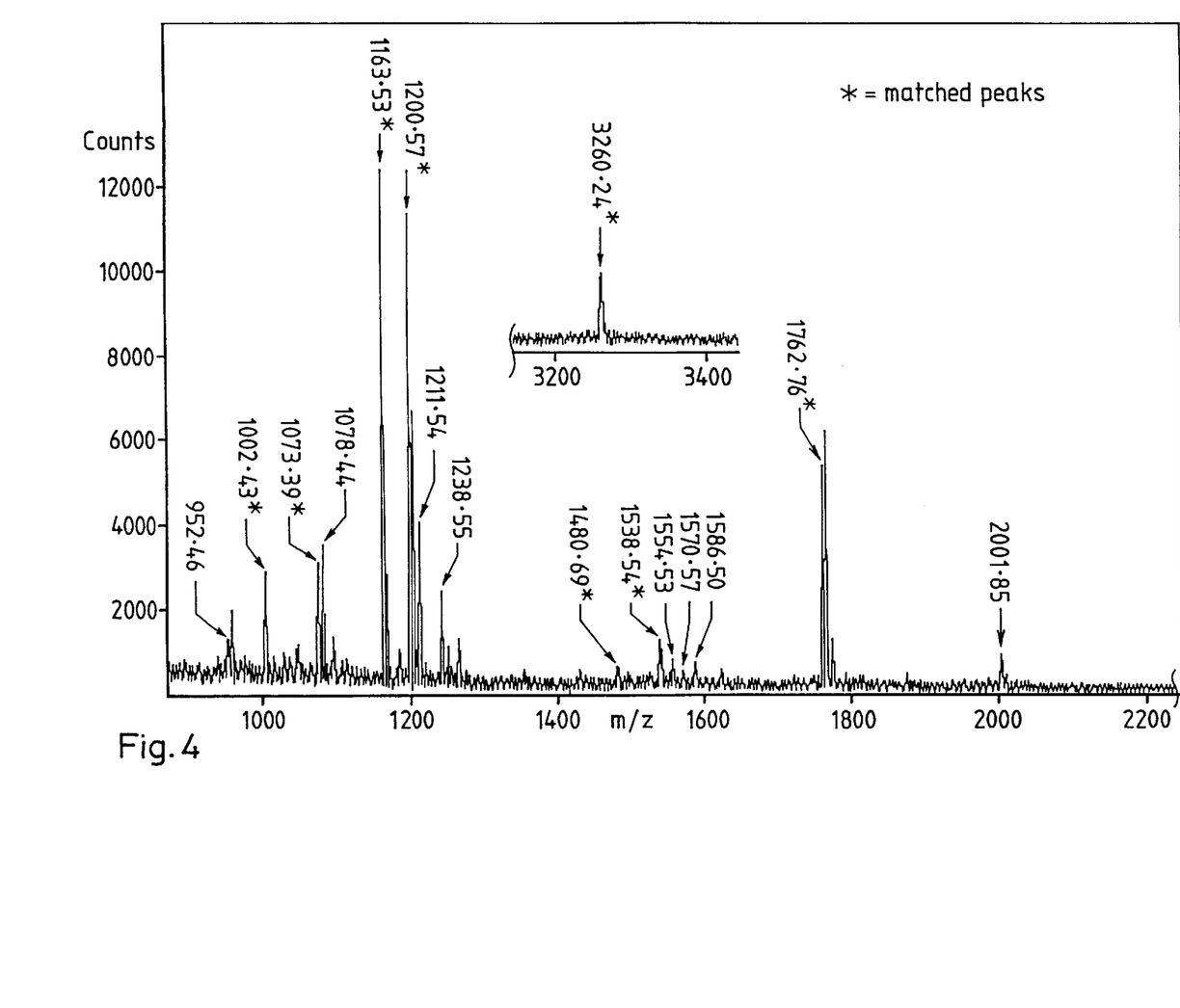
FIGS. 4 and 5 show the MALDI-TOF MS spectra obtained from soybean trypsin inhibitor and chicken ovalbumin respectively.
Figure 5:
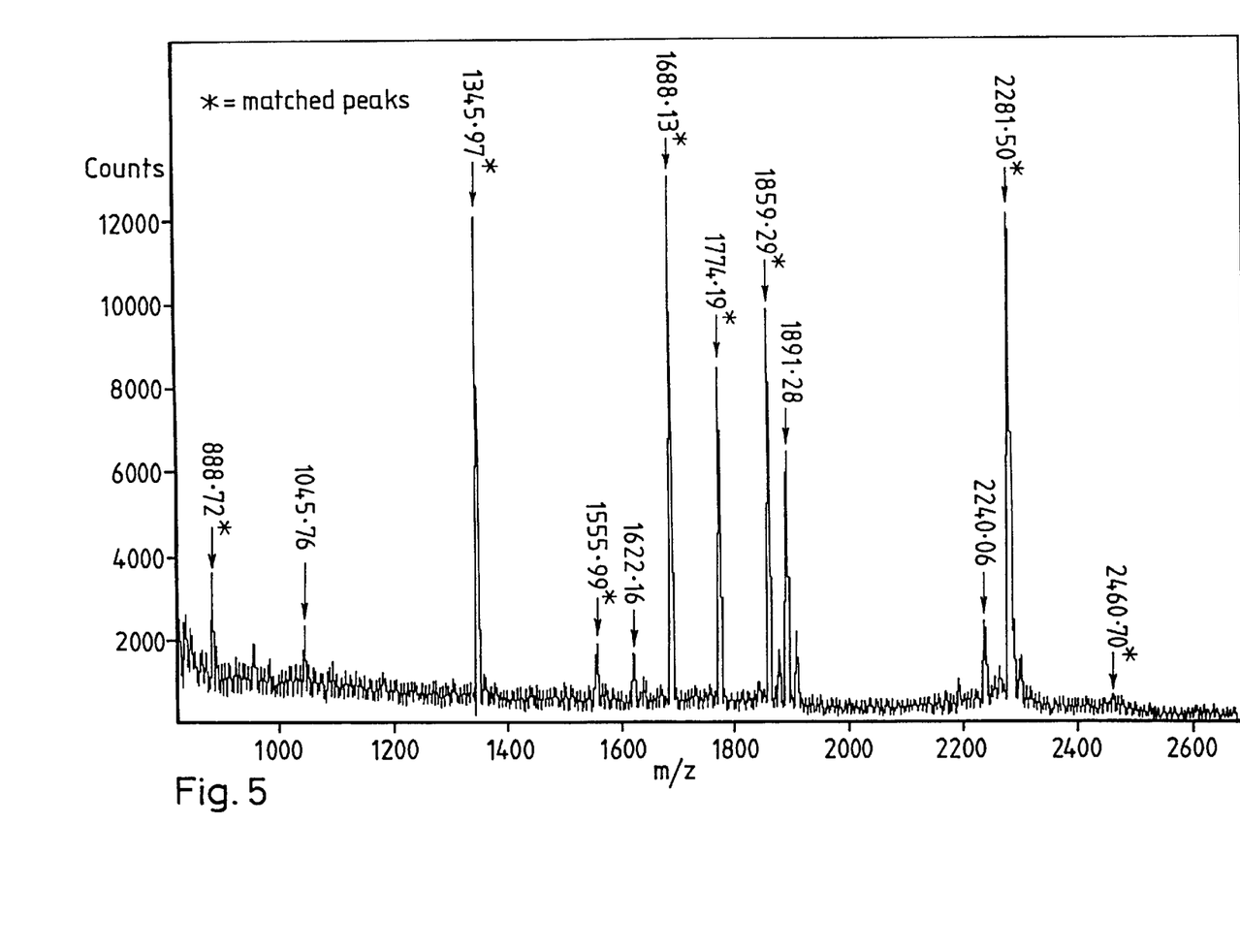

Transblot apparatus, procedure and buffer composition. Immediately after the SDS-PAGE protein separation, gels were soaked in deionized water for 5–10 minutes, and then equilibrated for 30 minutes in a half Towbin's buffer (13 mM Tris, 100 mM glycine, 10% methanol, pH 8.3). Electroblot transfer was carried out in half Towbin's buffer in a Mini-Trans-Blot electrophoretic transfer cell (Bio-Rad, Richmond, Calif., USA) for 16 hours at room temperature (21 to 24° C.) with a squared shape alternative applied voltage, periodically +12.5 V for 200 ms and −12.5 V for 50 ms. The shape of the applied voltage is shown in FIG. 3, in which voltage is plotted on the y-axis and time in milliseconds on the x-axis. The effective voltage $U_{eff}$=3.5 V and is given by the identity $$U_{eff} = \frac{1}{T} \times [Intergral\ between\ 0\ and\ T\ of\ Udt]$$

where U is the voltage at a particular timepoint, dt is the change in time and T is the total time during which the voltage is applied.

To perform the enzymatic digestion of the protein during the electroblotting, a double layer of IAV-trypsin membrane was placed between the polyacrylamide gel as a protein source and the PVDF membrane as the collecting surface to create a transblot-digestion sandwich (FIGS. 1 and 2). After the electroblotting transfer procedure, the PVDF collection membranes, i.e. on which the fragments of digested protein were collected, were washed in deionized water for 10 to 30 minutes. Proteins remaining in the gel after the electroblotting were stained with Coomassie Blue (0.1% w/v), methanol (30% v/v) and acetic acid (10% v/v) for 30 minutes. Gels were destained by repeated washing with methanol (40% v/v), and acetic acid (10% v/v) solution. The PVDF collection membranes were stained with amido black (0.5% w/v), isopropanol (25% v/v) and acetic acid (10% v/v) for 1 minute and then destained by repeated washing with deionized water. The membranes were air-dried before optical scanning.

MALDI-TOF equipment and experimental conditions. PVDF membranes were analyzed with a MALDI-TOF mass spectrometer "Voyager" Elite (PerSeptive Biosystems, Framingham Mass., USA) equipped with 337 nm nitrogen laser. The analyzer was used in the reflectron mode at an accelerating voltage of 3.8 kV, a delay of extraction of 140 ns and a low mass gate fixed at 800 Da. Laser power was set slightly above threshold for molecular ion production. Spectra were obtained by summation of 10 to 256 consecutive laser shots without any smoothing procedure (FIG. 4). Small pieces of the PVDF (1×1 mm square) and larger pieces (at least 40× at least 40 mm) containing the stained protein were cut from the PVDF collection membrane and fixed on an adaptable sample MALDI plate with silicon grease. For deposition of the matrix required for MALDI-TOF MS, 1 μl of 4 mg/ml α-cyano-4-hydroxycinnamic acid in 30% acetonitrile, 0.1% TFA solution was added to the anodic PVDF membrane. For the internal calibration, 0.5 μl each of 100 nM solutions of the following synthetic peptides (but which have amide terminations on their C-terminal carboxylic acid groups):

Arg Ala Phe His Thr Thr Gly Arg Ile Ile Ala Gly Ala Glu (SEQ ID NO: 1) and

Ser His Ser Ala Asp Val Arg Ala Phe His Thr Thr Gly Arg Ile Ile Ala Gly Ala Glu (SEQ ID NO: 2)

was added to the PVDF membrane before the complete air-drying of the matrix solution. External calibration was also used, also giving good accuracy of the peptide masses.

Spectra treatment, software utilization. Without distinction as to the calibration method, detected peaks were submitted to the peptide mass fingerprint search tool "PeptIdent" available on the World Wide Web (http://www.expasy.ch/www/tools.html) located at the ExPASy server (http:/www.expasy.ch) (FIG. 6). No mass and pI limits were introduced to restrict the search. Mass tolerance depended on the calibration methods i.e. ±0.5 Da with an external calibration and ±0.2 Da with an internal calibration). Cysteine and methionine modifications were chosen depending on the chemical treatment applied to the protein sample. When a potential protein was identified, unmatched fragment masses were submitted to "FindMod" (http://www.expasy.ch/www/tools.html) in order to search for post-translational modifications and/or single amino acid substitutions.

Results

Trypsin was attached covalently to IAV membranes with a surface enzyme density, as determined by TAME test, of 0.6 to 1.2 mg of active trypsin per $cm^2$. The activity of the trypsin-bound IAV membranes remained stable when they were stored in the Tris-HC1/$CaCl_2$/$NaN_3$ solution at 4° C. for periods up to a month. Tryptic activity decreased slightly after use of the membrane in the method of the invention, but not sufficiently to impair its re-use in another experiment.

Experiments wherein two trypsin-bound IAV membranes (TIAV) were interposed, one on top of another, between the polyacrylamide gel and the anodic PVDF membrane showed no obvious loss of protein nor loss of resolution during the electro-transfer procedures.

The alternating field, wherein the cycle provides positive and negative currents of unequal duration, apply during the blotting procedure provided good forward transblot of proteins onto the anodic membrane and no backward transfer to the cathodic membrane, as shown by amido black staining.

After SDS-PAGE separation, six proteins, rabbit phosphorylase b, bovine serum albumin (BSA), chicken ovalbumin, bovine carbonic anhydrase, soybean trypsin inhibitor and chicken lysozyme, run on the same track in the SDS-PAGE, were transblotted through two trypsin-bound IAV membranes onto a PVDF membrane, as shown in FIG. 2. The above proteins were correctly identified from the MALDI-TOF MS spectra of their peptide fragments automatically interpreted with "PeptIdent". "PeptIdent" gives probability scores, the highest result being for the most probable protein, the next highest score for the second most probable and so on.

Table 1 shows the information given by the monitor screen of a computer in the identification made by MALDI-TOF MS of the soybean trypsin inhibitor, with the aid of the PeptIdent program. Since the reproduction of the exact screen is incompatible with patent office typography or drawing requirements, the layout of Table 1 is not quite the same as on the screen, but the same information is conveyed in the Table. In the upper section, the user sets the search criteria, including the peptide mass peaks found in the MALDI-TOF MS. In the lower section, the mass found ("user mass") is compared with the known mass on a database (DB) and their difference (Δ mass) is also shown. "MC" denotes the number of modifications considered in arriving at the DB mass. represents the correct soybean trypsin inhibitor and was given the highest probability score. "CG21_SOYBN" is a completely soybean protein, given a lower probability score. "Cys_PAM: 63", "Cys_PAM: 167" and "Cys_PAM: 404", all in an additional column headed "Modification" on the screen (not shown here), mean that amino acids 63 of "ITRA_SOYBN" and 167 and 404 of "CG21_SOYBN" are cysteines which are assumed to be modified by being propionamidylated. This modification increases the molecular mass attributable to the cysteine residue by 71 units, corresponding to the removal of one H-atom and the addition of a propionamido group. Methionines can be oxidized to a sulfoxide, which shows as 1×MSO on the screen in the same "Modification" column and increases the assumed molecular mass by 16. The PeptIdent screen contains links to other screens through click boxes which are italicized and underlined in Table 1.

In Table 2, headed "Find Mod tool", the upper section contains two click words, shown here in underlined italics. In the lower section, "Matching peptides" repeats the ID information of Table 1. The section "Potentially modified peptides . . . . " shows the information given by the monitor screen of a computer in the identification of post-translational modifications of proteins made by MALDI-TOF MS, with the aid of the FindMod program, as applied to two peaks found in the soybean protein spectrum.

This section thus shows certain modifications which could account for the relative molecular masses revealed in the MALDI-TOF. The third column (mass diff.) shows the mass difference between the user and database masses, while the fourth column (Δ mass) compares this with the difference in molecular mass which would be accounted for by a modification (mod. diff.). Abbreviations used for the modifications are "HYDR"=hydroxylation, "METH"=methylation, "GLCN"=addition of OGlcNAc (OGlcNAc =N-acetyl-O-glucosaminyl) and "GERA"=addition of geranyl-geranyl. The first peptide (SEQ ID NO: 7) is already modified at the 138 methionine by oxidation, giving a DB mass 16 higher than the unoxidized peptide. This is noted by "MSO: 138" in an additional column on the screen (not shown here).

TABLE 1

| PeptIdent - Peptide Mass Fingerprinting | |
| --- | --- |
| Name given to unknown protein | Spot No. 2 |
| Species searched | PLANTA |
| Keyword | — |
| pI: 7 | range 3–17 |
| Mw 500000 | range 0–1000000 |
| Peptide masses for unknown protein | 952.46 1002.43 1073.39 1078.44 1163.53 1200.57 1238.55 1480.69 1538.54 1570.57 1586.50 1762.76 2001.85 3260.24 |
| Tolerance | ±0.5 Dalton |
| Minimum number of peptides required to match | 4 |

Using monoisotopic masses of the occurring amino acid residues and interpreting your peptide masses as [M +H]$^+$. Enzyme: trypsin allowing for up to 1 missed cleavage.

Cysteine treated with acrylamide.

Methionine in oxidized form.

Scan done on Jun. 15, 1998, SWISS-PROT Release 35 and updates to Jun. 13, 1998: 73459 entries.

| ITRA_SOYBN 1, PI 4.61, Mw 20094.68, Score 0.57, Hits 8 | | | | | |
| --- | --- | --- | --- | --- | --- |
| FindMod form | | | | Peptide Mass | |
| User mass | DB mass | Δ mass | MC | Peptide (a) | Position |
| 1002.43 | 1002.541 | 0.111 | 0 | CPLTwQSR | 63–71 |
| 1073.39 | 1073.541 | 0.151 | 0 | CPLTWSQR(b) | 63–71 |
| 1163.53 | 1163.642 | 0.112 | 0 | GIGTIISSPYR | 77–87 |
| 1200.57 | 1200.71 | 0.14 | 0 | NKPLVVQFQK | 190–199 |
| 1480.69 | 1480.864 | 0.174 | 1 | IRFIAEGHPLSLK | 88–100 |
| 1538.54 | 1538.706 | 0.166 | 1 | IGENKDAMDGWFR | 131–143 |
| 1762.76 | 1762.934 | 0.174 | 1 | NELDKGIGTIISSPYR | 72–87 |
| 3260.24 | 3260.575 | 0.335 | 0 | DFVLDNEGNPLENGGTYYILSDITAFGGIR | 25–54 |

| CG21_SOYBN, pI 9.02, Mw 50094.78, Score 0.28, Hits 4 | | | | | |
| --- | --- | --- | --- | --- | --- |
| FindMod form | | | | Peptide Mass | |
| User mass | DB mass | Δ mass | MC | Peptide (c) | Position |
| 1002.43 | 1002.541 | 0.111 | 0 | AACGITNKPK | 165–174 |
| 1073.39 | 1073.577 | 0.187 | 0 | AACGITNKPK (b) | 165–174 |
| 1762.76 | 1762.955 | 0.195 | 0 | RELQLVGISAMLMASK (d) | 266–281 |
| 3260.24 | 3260.571 | 0.331 | 0 | LHTGYSQEQLMDCARLLVGFYSTLENGK (b) (d) | 392–419 |

(a) SEQ ID NOS: 3, 3, 4, 5, 6, 7, 8 and 9.
(b) Cys with PAM modification: see text.
(c) SEQ ID NOS. 10, 10, 11 and 12.
(d) 1 × Met with MSO modification: see text

TABLE 2: Find Mod Tool

ITRA SOYBN (P01O070)
TRYPSIN INHIBITORS A AND C PRECURSOR (KUNITZ).
GLYCINE MAX (SOYBEAN).
Considered chain: CHAIN 25 205 TRYPSIN INHIBITOR A.
Theoretical pI/Mw 4.61/20094.68.
Calculate the theoretical masses of peptides generated by the chemical or enzymatic cleavage of this protein using PeptideMass.
Click here to see the mass values used in this program.

| | | | | Matching peptides | |
|---|---|---|---|---|---|
| User mass | DB mass | Δ mass | MC | Peptide (a) | Position |
| 1002.43 | 1002.541 | 0.111 | 0 | CPLTVVQSR | 63–71 |
| 1073.39 | 1073.541 | 0.151 | 0 | CPLTWSQR (b) | 63–71 |
| 1163.53 | 1163.642 | 0.112 | 0 | GIGTIISSPYR | 77–87 |
| 1200.57 | 1200.71 | 0.14 | 0 | NKPLWQFQK | 190–199 |
| 1480.69 | 1480.64 | 0.174 | 1 | IRFIAEGHPLSLK | 88–100 |
| 1538.54 | 1538.706 | 0.166 | 1 | IGENKDAMDGWFR | 131–143 |
| 1762.76 | 1762.934 | 0.174 | 1 | NELDKGIGTIISSPYR | 72–87 |
| 3260.24 | 3260.575 | 0.335 | 0 | DFVLDNEGNPLENGGTYYILSDITAFGGIR | 25–54 |

(a) SEQ ID NOS: 3, 3, 4, 5, 6, 7, 8, 9.
(b) Cys 63 with PAM modification: see text.

| | Potentially modified peptides, detected by mass difference and conforming to rules (considering only peptide masses that have not matched above) | | | | | | |
|---|---|---|---|---|---|---|---|
| User mass | DB mass | mass diff. | mod. diff | Δ mass | pot. mod. | MC | Peptide (c) |
| 1570.57 | 1554.701 | 15.869 | 15.995 | 0.126 | HYDR | 1 | IGENKDAMDGWFR (d) |
| 1570.57 | 1556.916 | 13.654 | 14.016 | 0.362 | METH | 1 | NKPLwQFQKLDK |
| 2001.85 | 1798.923 | 202.927 | 203.079 | 0.152 | GLCN | 1 | AAPTGNERCPLTVVQSR |
| 2001.85 | 1729.793 | 272.057 | 272.25 | 0.193 | GERA | 1 | CGDIGISIDHDDGTRR |

(c) SEQ ID NOS: 7, 13, 14, 15; additional column (not shown here) gives positions 131–143, 190–202, 55–71, 169–184.
(d) Met 138 with MSO modification: see text.

We claim:

1. A method of identifying polypeptides which have been separated by gel electrophoresis on the same gel, comprising:

a. providing adjacent to the gel a hydrophilic membrane on which is immobilized a cleaving reagent capable of cleaving a polypeptide, wherein the reagent generates fragments of the separated polypeptides;

b. providing a hydrophobic collection member suitable for receiving thereon the fragments of polypeptide transferred thereto by electroblotting, wherein said member is a film, membrane or support having a hydrophobic layer thereon, said hydrophobic member being positioned beyond the hydrophilic membrane in a direction of movement of the fragments of polypeptide;

c. electroblotting the polypeptides through the hydrophilic membrane, under conditions wherein the cleaving reagent cleaves the polypeptides into fragments which are collected on the hydrophobic member; and d. identifying the fragments collected on the hydrophobic member, wherein identification of the fragments, identifies the polypeptide from which they came.

2. The method of claim 1, wherein the cleaving reagent is immobilized by covalent bonding to the hydrophilic membrane.

3. A method of identifying polypeptides which have been separated by gel electrophoresis on the same gel, comprising:

a. providing adjacent to the gel a hydrophilic membrane on which is immobilized an enzyme capable of cleaving a polypeptide, wherein the enzyme generates fragments of the separated polypeptides;

b. providing a hydrophobic collection member suitable for receiving thereon the fragments of polypeptide transferred thereto by electroblotting, wherein said member is a film, membrane or support having a hydrophobic layer thereon, said hydrophobic member being positioned beyond the hydrophilic membrane in a direction of movement of the polypeptide fragments;

c. electroblotting the polypeptides from the separation gel through the hydrophilic membrane, under conditions wherein the enzyme cleaves the polypeptides into fragments which are collected on the hydrophobic member; and d. identifying the fragments collected on the hydrophobic membrane wherein identification of the fragments identifies the polypeptides from which they came.

4. The method of claim 3, wherein the enzyme cleaves the main chain of the polypeptide.

5. The method of claim 3, wherein the enzyme cleaves a side chain of the polypeptide.

6. The method of claim 1, wherein the electroblotting voltage is adjusted so as to extend the residence time of the polypeptide in the proximity of the cleaving reagent.

7. The method of claim 1, in which the electroblotting is carried out under conditions which provide either (1) a discontinuous current from anode to cathode or (2) an alternating current biased in the anode to cathode direction.

8. The method of claim 1, wherein the fragments are identified by time of flight mass spectrometry.

9. The method of claim 8, wherein the hydrophobic member is scanned directly by matrix-assisted laser desorption/ionization mass time of flight spectrometry and the data obtained therefrom compared with a database, using a computer program, to provide automated polypeptide identification.

* * * * *